US012583995B2

(12) United States Patent
Shimizu et al.

(10) Patent No.: US 12,583,995 B2
(45) Date of Patent: Mar. 24, 2026

(54) COMPOUND, CROSSLINKING AGENT AND CROSSLINKED FLUOROELASTOMER

(71) Applicants: NICHIAS CORPORATION, Tokyo (JP); KYOTO INSTITUTE OF TECHNOLOGY, Kyoto (JP)

(72) Inventors: Tomoya Shimizu, Tokyo (JP); Ayumi Toh, Tokyo (JP); Tsutomu Konno, Kyoto (JP)

(73) Assignees: NICHIAS CORPORATION, Tokyo (JP); KYOTO INSTITUTE OF TECHNOLOGY, Kyoto (JP)

( * ) Notice: Subject to any disclaimer, the term of this patent is extended or adjusted under 35 U.S.C. 154(b) by 835 days.

(21) Appl. No.: 17/785,821

(22) PCT Filed: Dec. 18, 2020

(86) PCT No.: PCT/JP2020/047531
§ 371 (c)(1),
(2) Date: Jun. 15, 2022

(87) PCT Pub. No.: WO2021/125347
PCT Pub. Date: Jun. 24, 2021

(65) Prior Publication Data

US 2023/0100818 A1 Mar. 30, 2023

(30) Foreign Application Priority Data

Dec. 19, 2019 (JP) ................................ 2019-229486

(51) Int. Cl.

| | |
|---|---|
| ***C08F 14/18*** | (2006.01) |
| ***C07C 35/50*** | (2006.01) |
| ***C07C 43/192*** | (2006.01) |
| ***C07C 43/196*** | (2006.01) |
| ***C08K 5/053*** | (2006.01) |
| ***C08K 5/06*** | (2006.01) |
| ***C08L 27/12*** | (2006.01) |

(52) U.S. Cl.
CPC ................ *C08K 5/06* (2013.01); *C07C 35/50* (2013.01); *C07C 43/192* (2013.01); *C07C 43/196* (2013.01); *C08K 5/053* (2013.01); *C08L 27/12* (2013.01); *C08F 14/18* (2013.01); *C08L 2312/00* (2013.01)

(58) Field of Classification Search
None
See application file for complete search history.

(56) References Cited

U.S. PATENT DOCUMENTS

| | | | | |
|---|---|---|---|---|
| 3,020,309 | A | 2/1962 | Luvisi | |
| 6,191,233 | B1 | 2/2001 | Kishine et al. | |
| 2005/0282969 | A1 | 12/2005 | Comino et al. | |
| 2016/0185892 | A1* | 6/2016 | Shimizu | C09K 3/1009 568/639 |
| 2017/0226255 | A1* | 8/2017 | Shimizu | C07C 22/08 |
| 2019/0153138 | A1 | 5/2019 | Shimizu et al. | |
| 2019/0270835 | A1 | 9/2019 | Shimizu et al. | |
| 2020/0148805 | A1 | 5/2020 | Shimizu et al. | |
| 2023/0174764 | A1* | 6/2023 | Shimizu | C08L 27/16 525/199 |

FOREIGN PATENT DOCUMENTS

| | | | |
|---|---|---|---|
| JP | 2006-009010 | A | 1/2006 |
| JP | 2016-145167 | A | 8/2016 |
| JP | 2016-145277 | A | 8/2016 |
| JP | 2017-081889 | A | 5/2017 |
| WO | WO-98/00407 | A1 | 1/1998 |
| WO | WO-2015/019581 | A1 | 2/2015 |

(Continued)

OTHER PUBLICATIONS

Cobb et al., "Dimers of Cyclobutene-1,2-dicarbonitrile and 1,3-Butadiene-2,3-dicarbonitrile. Preparation and Chemistry", Journal of Organic Chemistry, 1977, pp. 2601-2610, vol. 42, No. 15.

Kazmina et al., "Thermal reactions of hexafluoro-1,3-butadiene. Part I. Primary products and their thermal transformations", Journal of Fluorine Chemistry, 1993, pp. 57-83, vol. 61, 1993—Elsevier Sequoia.

(Continued)

*Primary Examiner* — Richard A. Huhn
(74) *Attorney, Agent, or Firm* — Foley & Lardner LLP

(57) ABSTRACT

The present invention provides a crosslinking agent which can improve crosslinked fluoroelastomer high-temperature vapor resistance and a crosslinked fluoroelastomer having improved high-temperature vapor resistance. The present invention provides a compound having a structure represented by the following formula (1) (in the formula, $R^1$ to $R^6$ are each a hydrogen atom, a substituent, or a leaving group, and two or more of $R^1$ to $R^6$ are leaving groups; $R^a$ to $R^c$ are each a hydrogen atom or a substituent; and n is an integer from 2 to 5).

(1)

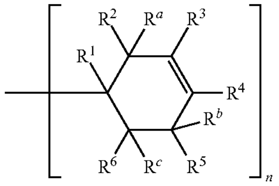

7 Claims, No Drawings

(56) References Cited

FOREIGN PATENT DOCUMENTS

WO WO-2016/017187 A1 2/2016

OTHER PUBLICATIONS

International Search Report issued in PCT Application No. PCT/JP2020/047531, mailed Mar. 16, 2021.

Office Action for JP Application No. 2023-109200 dated Jun. 27, 2024, 6 pages. English Translation.

* cited by examiner

COMPOUND, CROSSLINKING AGENT AND CROSSLINKED FLUOROELASTOMER

CROSS REFERENCE TO RELATED APPLICATIONS

This application is a national stage entry of PCT Application No. PCT/JP2020/047531, filed on Dec. 18, 2020, which claims priority to Japanese Application No. 2019-229486, filed on Dec. 19, 2019, the contents of all of which are incorporated herein by reference in their entireties.

TECHNICAL FIELD

The present invention relates to a novel compound useful as a crosslinking agent and to a crosslinked fluoroelastomer obtained using said crosslinking agent.

BACKGROUND ART

A sealing material made from a crosslinked fluoroelastomer is used as a sealing material having suitable heat resistance, vapor resistance, and rapid decompression resistance. Various crosslinking agents are known as crosslinking agents of crosslinked fluoroelastomers. Examples include triallyl isocyanurate (TAIC) and 1,6-divinylperfluorohexane (see patent documents 1 and 2).

In recent years, power plants have tended to increase the temperature of steam to above that which is conventional with the aim of increasing power generation efficiency, accompanying which, sealing materials also require durability against the high-temperature steam.

PRIOR ART DOCUMENTS

Patent Documents

Patent Document 1: WO 98/00407

Patent Document 2: JP 2006-9010 A

SUMMARY OF INVENTION

A fluoroelastomer, which acts as a base material of a crosslinked fluoroelastomer, has sufficient high-temperature vapor resistance. Meanwhile, the crosslinking points in patent documents 1 and 2, which are binding sites between the crosslinking agent and the fluoroelastomer, have many bonds which are weak to heat and vapor and thus cannot be said to have sufficient high-temperature vapor resistance, which is a cause of decomposition and degradation.

One object of the present invention is to provide a crosslinking agent which can improve crosslinked fluoroelastomer high-temperature vapor resistance and a crosslinked fluoroelastomer having improved high-temperature vapor resistance.

According to the present invention, the following compounds and the like are provided.

1. A compound having a structure represented by the following formula (1)

[Formula 1]

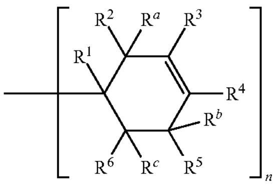

(1)

(in the formula, $R^1$ to $R^6$ are each a hydrogen atom, a substituent, or a leaving group, and two or more of $R^1$ to $R^6$ are leaving groups; $R^a$ to $R^c$ are each a hydrogen atom or a substituent; and n is an integer from 2 to 5).

2. The compound according to 1, being a compound represented by the following formula (2A)

[Formula 2]

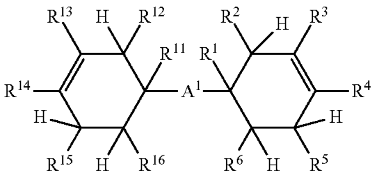

(2A)

(in the formula, $R^1$ to $R^6$ and $R^{11}$ to $R^{16}$ are each a hydrogen atom, a substituent, or a leaving group, two or more of $R^1$ to $R^6$ are leaving groups, and at least two of $R^{11}$ to $R^{16}$ are leaving groups; and $A^1$ is a single bond or a linking group).

3. The compound according to 2, being a compound represented by the following formula (2B)

[Formula 3]

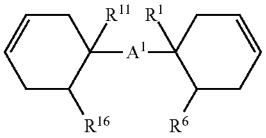

(2B)

(in the formula, $R^1$, $R^6$, $R^{11}$, and $R^{16}$ are each a leaving group; and $A^1$ is as in formula (2A)).

4. The compound according to 2 or 3, wherein $A^1$ is a single bond, —O—, —S—, a heteroatom-containing group, a linear alkene group, a branched alkene group, a cycloalkene group, a fluorinated alkene group, or an arylene group.
5. The compound according to any of 1 to 4, wherein the leaving group is a group selected from a halogen atom, a hydroxyl group, an alkoxy group, a carbonyl-containing group, a phosphorus-containing substituent, a sulfur-containing substituent, primary to tertiary amino group, a cyano group, and a nitro group.
6. A crosslinking agent containing the compound according to any of 1 to 5.
7. A composition containing a fluoroelastomer, a crosslinking initiator, and the crosslinking agent according to 6.
8. A crosslinked fluoroelastomer obtained by crosslinking the composition according to 7.

9. A method for producing a crosslinked fluoroelastomer, including a step for heating the composition according to 7 to react the fluoroelastomer with the crosslinking agent and a step for converting a cyclohexane ring derived from the crosslinking agent into an aromatic ring.
10. A crosslinked fluoroelastomer produced by the method in 9, wherein a gel fraction after being exposed to 330° C. saturated steam for 24 hours is 45% or more.
11. A crosslinked fluoroelastomer, wherein a gel fraction after being exposed to 330° C. saturated steam for 24 hours is 45% or more.
12. The crosslinked fluoroelastomer according to 11, wherein the crosslinked structure does not contain any unsaturated bonds other than those in aromatic rings.
13. A molded product obtained from the crosslinked fluoroelastomer according to any of 8 and 10 to 12.
14. The molded product according to 13, being a sealing material.

According to the present invention, it is possible to provide a crosslinking agent which can improve crosslinked fluoroelastomer high-temperature vapor resistance and a crosslinked fluoroelastomer having improved high-temperature vapor resistance.

EMBODIMENTS OF THE INVENTION

[Compound and Crosslinked Product]

The compound according to one embodiment of the present invention has a structure represented by the following formula (1)

[Formula 4]

(1)

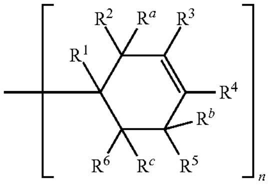

(in the formula, $R^1$ to $R^6$ are each a hydrogen atom, a substituent, or a leaving group, and two or more of $R^1$ to $R^6$ are leaving groups; $R^a$ to $R^c$ are each a hydrogen atom or a substituent; and n is an integer from 2 to 5).

The compound of the present embodiment is useful as, for example, a crosslinking agent. In the foregoing structure, the double bond of the cyclohexene ring reacts with a reaction site of a fluoroelastomer and forms a structure in which the fluoroelastomer and the cyclohexane ring are directly bound. Then, by converting the cyclohexane ring into an aromatic ring, high-temperature vapor resistance improves compared to a conventional crosslinked structure, for example, a crosslinked structure obtained using a crosslinking agent having a vinyl group or a fluorovinyl group, as no bonds weak to heat or vapor are included.

In formula (1), $R^1$ to $R^6$ are each a hydrogen atom, a substituent, or a leaving group.

The substituent is any group other than the leaving group described later and is not particularly limited insofar as it is a group which does not hinder the effect of the invention of the present application. Examples include an alkyl group, a cycloalkyl group, an aryl group, and the like.

The alkyl group may be linear or branched and preferably has 1 to 15 carbons (more preferably 1 to 6 carbons). The cycloalkyl group preferably has 3 to 8 carbons (more preferably 3 to 6 carbons). The aryl group preferably has 6 to 18 carbons (more preferably 6 to 12 carbons). Examples of the aryl group include a phenyl group, a naphthyl group, and the like.

Some or all of the carbon atoms of the substituent may be fluorinated.

The leaving group is a group having a function of leaving the cyclohexane ring by an operation such as heating to convert the cyclohexane ring into an aromatic ring. Specific examples include a halogen atom, a hydroxyl group, an alkoxy group, a carbonyl-containing group, a phosphorus-containing substituent, a sulfur-containing substituent, primary to tertiary amino group, a cyano group, a nitro group, and the like.

Examples of the halogen atom include, I, Br, Cl, F, and the like.

The alkoxy group is a group represented by $—OR^{x1}$, and examples of R include an alkyl group, a cycloalkyl group, an aryl group, and the like. It is preferably an alkyl group such as a methyl group, an ethyl group, and n-propyl group, or an isopropyl group.

The carbonyl-containing group is preferably a formyl group, a carboxyl group, a carbonyl group represented by $—C(=O)R^{x2}$, or an alkoxycarbonyl group represented by $—C(=O)OR^{x2}$. Examples of $R^{x2}$ include an alkyl group, a cycloalkyl group, an aryl group, and the like.

$R^{x2}$ is preferably an alkyl group such as a methyl group, an ethyl group, and n-propyl group, or an isopropyl group.

Examples of the phosphorus-containing substituent include a phosphoryl group, a phosphinyl group, a phosphanyl group, and the like.

Examples of the sulfur-containing substituent include a sulfonate group, a sulfonyl group, a sulfinyl group, a sulfenyl group, a mercapto group, and the like.

Specifically, the sulfonyl group is preferably a group represented by $—S(=O)_2R^{x3}$, the sulfinyl group is preferably a group represented by $—S(=O)R^{x3}$, and the sulfenyl group is preferably a group represented by $—SR^{x3}$. Examples of $R^{x3}$ include an alkyl group, a cycloalkyl group, an aryl group, and the like.

$R^{x3}$ is preferably an alkyl group such as a methyl group, an ethyl group, and n-propyl group, or an isopropyl group.

The leaving group is particularly preferably a hydroxyl group or an alkoxy group.

In one embodiment, the compound having the structure represented by formula (1) is represented by the following formula (2)

[Formula 5]

(2)

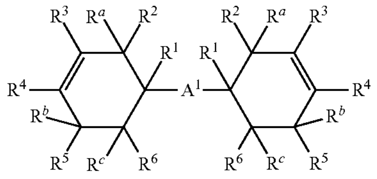

(in the formula, $R^1$ to $R^6$ and $R^a$ to $R^c$ are the same as in formula (1); $A^1$ is a single bond or a linking group; and two of $R^1$ to $R^6$ and $R^a$ to $R^c$ may be the same or may be different).

Examples of the linking group include —O—, —S—, a heteroatom-containing group, a linear alkene group, a branched alkene group, a cycloalkene group, a fluorinated alkene group, an arylene group, and the like.

The linear or branched alkene group preferably has 1 to 15 carbons (more preferably 1 to 6 carbons). The cycloalkene group preferably has 3 to 8 carbons (more preferably 3 to 6 carbons). The arylene group preferably has 6 to 18 carbons (more preferably 6 to 12 carbons).

Some or all of these groups may be fluorinated. For example, the cycloalkene group or the arylene group is fluorinated.

Examples of the alkene group include a methylene group, an ethylene group, a propene group, and the like. Examples of the arylene group include a phenylene group, a naphthalene group, and the like.

The fluorinated alkene group is a group in which some or all of the hydrogen atoms of the alkene group are fluorinated. It is preferably $-(CF_2)_m-$ (in the formula, m is in integer from 1 to 15 (preferably from 1 to 6)).

Furthermore, in one embodiment, the compound having the structure represented by formula (1) is represented by the following formula (3)

[Formula 6]

(3)

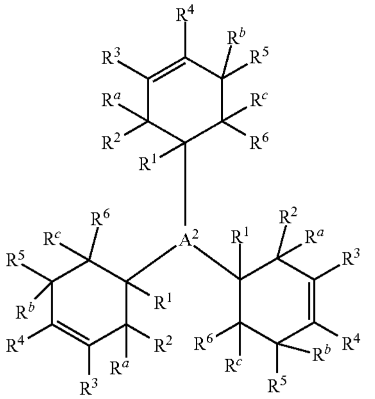

(in the formula, $R^1$ to $R^6$ and $R^a$ to $R^c$ are the same as in formula (1); $A^2$ is a linking group; and three of $R^1$ to $R^6$ and $R^a$ to $R^c$ may be the same or may be different).

Examples of the linking group include those capable of forming three bonds with the structure represented by formula (1), such as a boron atom (B), ≡C—H, a cycloalkene ring, an aromatic ring, a heterocyclic ring, or an aromatic heterocyclic ring.

A compound represented by the following formula (2A) is preferable as the compound of the present embodiment.

[Formula 7]

(2A)

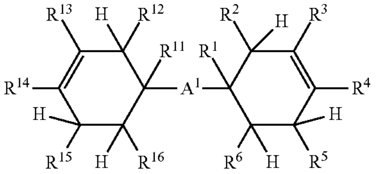

(in the formula, $R^1$ to $R^6$ and $R^1$ to $R^{16}$ are each a hydrogen atom, a substituent, or a leaving group, two or more of $R^1$ to $R^6$ are leaving groups, and at least two of $R^{11}$ to $R^{16}$ are leaving groups; and $A^1$ is a single bond or a linking group).

Furthermore, a compound represented by the following formula (2B) is preferable.

[Formula 8]

(2B)

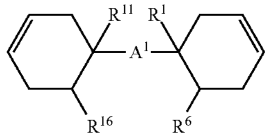

(in the formula, $R^1$, $R^6$, $R^{11}$, and $R^{16}$ are each a leaving group; and $A^1$ is as in formula (2)).

In formula (2B), hydrogen atoms bound to the cyclohexene ring are omitted.

A specific example of the compound of the present embodiment is illustrated below.

[Formula 9]

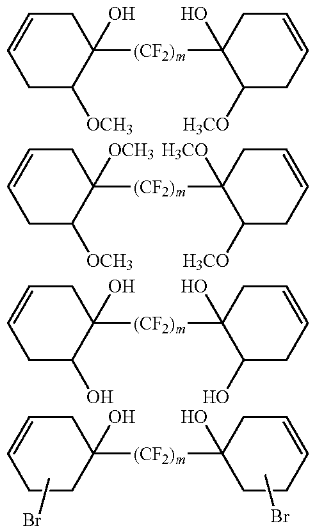

(In the formula, m is in integer from 1 to 15 (preferably from 1 to 6).)

The compound of the present embodiment may, for example, be synthesized by referring to the examples described later.

[Composition]

The composition according to the present embodiment contains the crosslinking agent (compound) described above, a fluoroelastomer, and a crosslinking initiator.

The crosslinking agent is preferably added in a range of 0.5 to 50 mmol with respect to 100 g of the fluoroelastomer, more preferably 0.5 to 40 mmol, more preferably 1 to 30 mmol, more preferably 1 to 25 mmol, and further preferably 2.0 to 20 mmol. The greater the amount added, the more the vapor resistance and the heat resistance tend to improve. However, when too great, there is a risk of hardening.

The fluoroelastomer may be a perfluoroelastomer or may be a partially fluorinated elastomer.

Examples include repeating units derived from the following monomers. A repeating unit derived from one or two of the following monomers may be included.

$CF_2{=}CH_2$ (vinylidene fluoride),
$CF_2{=}CF_2$ (tetrafluoroethylene),
$CF_2{=}CFCF_3$ (hexafluoropropylene),
$CH_2{=}CH_2$, and
$CH_2{=}CHCH_3$ The fluoroelastomer used in the present embodiment preferably includes an iodine atom and/or a bromine atom as a radical attack site during crosslinking (curing), more preferably an iodine atom. A perfluoroelastomer curable by a peroxide is taught in, for example, JP 2006-9010 A, and the like.

The (per)fluoroelastomer typically includes 0.001 wt % to 5 wt % of iodine with respect to the total polymer weight, preferably 0.01 wt % to 2.5 wt %. The iodine atoms may be present along chains and/or at terminal sites.

The (per)fluoroelastomer is preferably produced from a copolymer such as a (per)fluorinated olefin having one ethene-type unsaturated bond at the terminal site.

Examples of comonomers include the following.

$CF_2{=}CFOR_{2f}$ (per)fluoroalkyl vinyl ethers (PAVE)

(In the formula, $R_{2f}$ is a (per)fluoroalkyl group having 1 to 6 carbons, for example, a trifluoromethyl group or a pentafluoropropyl group.)

$CF_2{=}CFOX_o$(per)fluoroxy alkyl vinyl ethers (In the formula, $X_o$ is a (per)fluoroxy alkyl group having 1 to 12 carbons which includes one or more ether groups, for example, a perfluoro-2-propoxypropyl group.)

$$CFX_2{=}CX_2OCF_2OR''_f \quad \text{(I-B)}$$

(In the formula, $R''_f$ is a linear or branched (per)fluoroalkyl group having 2 to 6 carbons, a cyclic (per)fluoroalkyl group having 5 or 6 carbons, or a linear or branched (per)fluoroxy alkyl group having 2 to 6 carbons which includes 1 to 3 oxygen atoms, and $X_2$ is F or H.)

The (per)fluoro vinyl ether in formula (I-B) is preferably represented by the following formula.

$$CFX_2{=}CX_2OCF_2OCF_2CF_2Y \quad \text{(II-B)}$$

(In the formula, Y is F or $OCF_3$, and $X_2$ is as defined above.)

The perfluoro vinyl ethers in the following formulas are more preferable.

$$CF_2{=}CFOCF_2OCF_2CF_3 \text{ (MOVE1)}$$

$$CF_2{=}CFOCF_2OCF_2CF_2OCF_3 \text{ (MOVE2)}$$

Examples of preferable monomer compositions include the following.

Tetrafluoroethylene (TFE): 50 to 85 mol %, PAVE: 15 to 50 mol %;

TFE: 50 to 85 mol %, MOVE: 15 to 50 mol %.

The fluoroelastomer may include a vinylidene fluoride-derived unit, a fluoroolefin having 3 to 8 carbons and which may include a chlorine atom and/or a bromine atom, and a non-fluorinated olefin having 3 to 8 carbons.

The crosslinking initiator may be one which is normally used. Examples include peroxides, azo compounds, and the like.

The crosslinking initiator is preferably added in a range of 0.3 to 35 mmol with respect to 100 g of the fluoroelastomer, more preferably 1 to 15 mmol, and further preferably 1.5 to 10 mmol. The greater the amount added, the more the vapor resistance and the heat resistance tend to improve. However, when too great, scorching or bubbling may occur.

In one embodiment, the composition may include a crosslinking adjuvant.

Examples of the crosslinking adjuvant include zinc oxide, activated alumina, magnesium oxide, quaternary ammonium salts, quaternary phosphonium salts, amines, and the like. Including a crosslinking adjuvant improves crosslinking efficiency and heat resistance. Normally, 0.1 to 10 g of the crosslinking adjuvant is added to 100 g of the fluoroelastomer.

In one embodiment, the composition may include an aromatization accelerator.

Examples of the aromatization accelerator include acids and bases.

Either an organic acid or an inorganic acid may be used as the acid. Carbonic acid, sulfonic acid, and the like are preferable organic acids. Sulfuric acid, hydrochloric acid, nitric acid, phosphoric acid, boric acid, chromic acid, oxoacid, hydrogen halide, thionyl chloride, and the like are preferable inorganic acids.

Examples of bases include hydroxides, primary to tertiary amines, oxides, and the like.

Either one of an acid or a base may be added, or both may be reacted in advance and added as a salt.

Normally, 0.1 to 10 g of the aromatization accelerator is added to 100 g of the fluoroelastomer.

Furthermore, a filler may be added to the composition to increase mechanical strength. A filler generally known as an elastomer filler may be used insofar as it does not hinder the effect of the present invention. Examples include carbon black, silica, barium sulfate, titanium dioxide, semi-crystalline fluoropolymers, perfluoropolymers, and the like.

Furthermore, suitable amounts of thickeners, pigments, coupling agents, antioxidants, stabilizers, and the like may also be added as necessary.

[Crosslinked Fluoroelastomer and Molded Product]

The crosslinked fluoroelastomer according to the present embodiment is obtained by crosslinking the composition described above. For example, it is produced by a method having the following steps 1 and 2.

Step 1: A step for heating the foregoing composition to react the fluoroelastomer with the crosslinking agent Step 2: A step for converting a cyclohexane ring derived from the crosslinking agent into an aromatic ring The heating conditions in the foregoing step 1 may be set as appropriate according to the crosslinking agent used and the like. Generally, the heating temperature is 100 to 200° C., and the heating time is 5 to 60 minutes.

Due to this step, the fluoroelastomer and the crosslinking agent react and bind. As a result, the cyclohexene ring in the crosslinking agent becomes a cyclohexane ring.

Step 1 may, for example, be performed while the composition is inserted in a mold and pressed.

In step 2, the cyclohexane ring formed in step 1 is converted to an aromatic ring. The heating conditions may be adjusted as appropriate according to whether an aromatization accelerator is used, and the like. For example, heating is performed at 100 to 350° C. for 1 to 100 hours. This heating may be performed using an electric furnace or the like.

Note that a method having the foregoing steps 1 and 2 is indicated as one example of a production method, but it is not limited thereto. For example, by optimizing the heating conditions and the like, it may be possible to perform the foregoing steps 1 and 2 together.

The heating may be performed in an inert gas atmosphere or in air.

Nitrogen, helium, argon, and the like may be used as the inert gas, and nitrogen is preferable. In the inert gas atmosphere, the oxygen concentration is preferably 10 ppm or less, more preferably 5 ppm or less.

The crosslinked fluoroelastomer according to the present embodiment preferably does not include any unsaturated bonds other than those in aromatic rings.

Furthermore, a gel fraction of the crosslinked fluoroelastomer according to the present embodiment after being exposed to 330° C. saturated steam for 24 hours is preferably 35% or more, more preferably 45% or more. The gel fraction can be calculated by the following formula by measuring a mass (a) of the crosslinked fluoroelastomer prior to exposure to the saturated steam and a mass (B) of a solid portion remaining after immersing the crosslinked fluoroelastomer exposed to the saturated steam for 24 hours in a solvent (for example, Fluorinert FC-3283 (3M)).

Gel fraction=mass (B)/mass (A)×100

The crosslinked fluoroelastomer obtained by the foregoing method may be used as a sealing material and may be formed into a molded product such as an O ring, a gasket, or a sealing ring.

EXAMPLES

Vapor Resistance Calculation Results of Crosslinked Structure Model

The activation energy required for the water molecules to react was found using molecular orbital calculation. The results are shown in Table 1. Calculation was performed using Gaussian 09W (Rev. C.01) and a basis set of B3LYP/6-31+G*. The reaction with vapor becomes more difficult as the activation energy increases, and it can be said that it is a crosslinked structure having high high-temperature vapor resistance. The crosslinked structure (i) that can be derived from the crosslinking agent of the present invention has high activation energy and excels in vapor resistance because it does not include unsaturated bonds other than those in aromatic rings. Meanwhile, the crosslinked structures (ii) and (iii) derived from conventional crosslinking agents have low activation energy and poor vapor resistance because they include unsaturated bonds that are weak against vapor such as the vinyl group.

TABLE 1

Table 1: Vapor Resistance Calculation Results of Crosslinked Structure Model

| | Crosslinked Structure Model | Activation Energy [kcal/mol] |
|---|---|---|
| (i) | 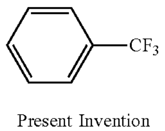 Present Invention | 59 |
| (ii) | 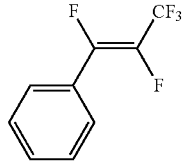 [SMILES: F/C(=C(/F)C(F)(F)F)c1ccccc1] | 45 |
| (iii) | 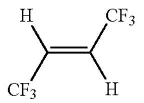 | 35 |

Example 1

Synthesis of Compound 1

Compound 1 described below was synthesized. Note that commercially available reagents were used for both the compound and the catalyst.

[Formula 10]

Compound 1

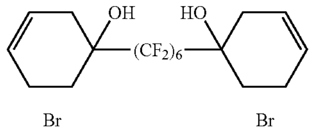

(1) Synthesis of Intermediate 1

Magnesium chips (1.10 g, 45.3 mmol) and diethyl ether (20 mL) were prepared in a 200 mL two mouth flask having an agitator installed in a nitrogen atmosphere. 4-Bromo-1-butene (5.43 g, 40.2 mmol) dissolved in diethyl ether (20 mL) was slowly added dropwise into this flask while being agitated at room temperature. This was then agitated for a further thirty minutes at room temperature.

The obtained solution (34 mL, 20.4 mmol) was prepared in a separate 100 mL two mouth flask in a nitrogen atmosphere and dodecafluorosuberic acid (1.57 g, 4.0 mmol) dissolved in diethyl ether (4 mL) was then slowly added dropwise into this flask while being agitated at room temperature. After dripping, this was agitated for 1.25 hours at 45° C., returned to room temperature, then agitated for 15 hours. After slowly adding 50% hydrochloric acid having ice added thereto, and the organic layer was extracted using diethyl ether (15 mL×three times). After the organic layer was washed using a saturated sodium hydrogen carbonate solution (20 mL×three times) and water (20 mL×three times), then dried using anhydrous sodium sulfate, a filtrate was concentrated under reduced pressure. The obtained concentrate was purified using silica gel chromatography to obtain 1.19 g of intermediate 1 below, being a diketone compound.

[Formula 11]

Intermediate 1

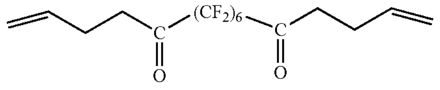

(2) Synthesis of Intermediate 2

Magnesium chips (0.53 g, 21.9 mmol) and diethyl ether (10 mL) were prepared in a 50 mL two mouth flask having an agitator installed in a nitrogen atmosphere, and allyl bromide (2.43 g, 20.1 mmol) dissolved in diethyl ether (10 mL) was slowly added dropwise into this flask while being agitated at room temperature. This was then agitated for a further thirty minutes at room temperature.

The obtained solution (11 mL, 6.3 mmol) was prepared in a separate 30 mL two mouth flask in a nitrogen atmosphere and cooled to −78° C. Intermediate 1 (1.19 g) dissolved in diethyl ether (2 mL) was slowly added dropwise into this flask while being agitated at −78° C. After agitating for 1 hour, returning to room temperature, and adding a reaction liquid into 10% hydrochloric acid, the organic layer was extracted using diethyl ether (15 mL×three times). After the organic layer was dried using anhydrous sodium sulfate, a filtrate was concentrated under reduced pressure. The obtained concentrate was purified using silica gel chromatography to obtain 1.13 g of intermediate 2 below, being a diol compound.

[Formula 12]

Intermediate 2

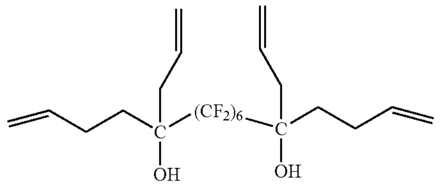

(3) Synthesis of Intermediate 3

Intermediate 2 (1.13 g, 2.05 mmol), dichloromethane (41 mL), and first generation Grubbs catalyst (0.086 g, 0.105 mmol) were prepared in a 100 mL two mouth flask having an agitator installed in a nitrogen atmosphere, and this was agitated for 21 hours at 50° C. After returning to room temperature, the reaction liquid was purified using silica gel chromatography to obtain 0.853 g of intermediate 3 below.

[Formula 13]

Intermediate 3

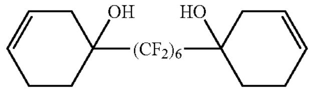

A structure analysis was performed on the obtained compound using $^{1}$H-NMR and $^{19}$F-NMR (AVANCE II 400 made by BRUKER). The results are shown below.

$^{1}$H-NMR ($CDCl_3$, 400 MHz): δ=1.79 (td, J=25.30 Hz, 6.07 Hz, 2H), 1.90 to 2.08 (m, 2H), 1.97 (s, 2H), 2.09 to 2.37 (m, 6H), 2.57 (d, J=17, 41 Hz, 2H), 5.53 to 5.67 (m, 2H), 5.73 to 5.86 (m, 2H)

$^{19}$F-NMR ($CDCl_3$, $CFCl_3$, 376 MHz): δ=−119.60 (d, J=8.70 Hz, 4F), −121.09 to −125.29 (m, 4F), −121.82 to −122.30 (m, 4F)

(4) Synthesis of Compound 1

Compound 1 (0.148 g, 0.3 mmol), N-bromosuccinimide (0.112 g, 0.63 mmol), azobisisobutyronitrile (AIBN: 0.0014 g, 0.009 mmol), and carbon tetrachloride (3 mL) were prepared in a 30 mL two mouth flask having an agitator installed in an argon atmosphere, and this was agitated for 2 hours at 80° C. After returning to room temperature, this was concentrated under reduced pressure, and the obtained concentrate was purified using silica gel chromatography to obtain compound 1.

It was confirmed that compound 1 was synthesized by $^{1}$H-NMR, $^{19}$F-NMR, and mass spectrometry (MS). The same is true of the compounds below.

Example 2

Synthesis of Compound 2

Compound 2 described below was synthesized.

[Formula 14]

(Compound 2)

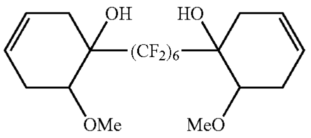

(In the formula, Me is the methyl group)

1,4-cyclohexadiene (8.01 g, 100.0 mmol) and dichloromethane (250 mL) were prepared in a 500 mL two mouth flask having an agitator installed in a nitrogen atmosphere, meta-chloroperoxybenzoic acid (containing 23% water, 23.55 g, 105.1 mmol) was slowly added while agitating at 0° C., and this was agitated for 48 hours at room temperature. After agitating, a sodium carbonate solution (2.5 M, 100 mL) was added and agitated for 15 minutes at 0° C. Next, after increasing the temperature to room temperature, the organic layer was washed using a saturated sodium hydrogen carbonate solution (200 mL) and a 20% saline solution (100 mL×three times), then dried using anhydrous sodium sulfate, and a filtrate was then concentrated under reduced pressure to obtain 6.62 g of a colorless, transparent liquid of 1,2-epoxy-4-cyclohexene.

Next, the 1,2-epoxy-4-cyclohexene described above (8.63 g, 89.8 mmol), methanol (180 mL), and 2,3-dichloro-5,6-dicyano-p-benzoquinone (0.509 g, 2.2 mmol) were prepared in a 500 mL two mouth flask having an agitator installed in a nitrogen atmosphere, and this was agitated for 17 hours at room temperature. After agitating and concentrating under reduced pressure, the obtained concentrate was purified using silica gel chromatography to obtain 8.43 g of light yellow oily 1-hydroxy-2-methoxy-4-cyclohexene.

Next, the 1-hydroxy-2-methoxy-4-cyclohexene described above (2.95 g, 22.9 mmol), acetonitrile (115 mL), potassium peroxymonosulfate (12.69 g, 20.6 mmol), and 2-iodo-5-nitro-sodium benzenesulfonate (0.804 g, 2.29 mmol) were prepared in a 500 mL two mouth flask having an agitator installed in a nitrogen atmosphere, and this was agitated for 14 hours at 70° C. After returning this to room temperature and removing the salt using a silica gel short column (diethyl ether), this was concentrated under reduced pressure. The concentrate was purified using silica gel chromatography to obtain 0.913 g of light yellow oily 2-methoxy-4-cyclohexene-1-one.

1,6-diiodododecafluorohexane (0.111 g, 0.2 mmol) and diethyl ether (2.5 mL) were prepared in a 30 mL two mouth flask having an agitator installed in an argon atmosphere, ethyl magnesium bromide (3.0 M: diethyl ether solvent, 0.146 mL, 0.44 mmol) was added dropwise while agitating at −78° C., and this was agitated for one hour and a half at −78° C. Thereafter, 2-methoxy-4-cyclohexene-1-one (0.0555 g, 0.44 mmol) was dissolved in diethyl ether (1.0 mL) and added dropwise, and this was agitated for 18 hours. After adding a saturated ammonium chloride aqueous solution, this was returned to room temperature, organic material was extracted from the water layer using diethyl ether, and the organic layer was dried using anhydrous sodium sulfate. The anhydrous sodium sulfate was removed by filtration, and after the organic layer was concentrated under reduced pressure, the obtained concentrate was then purified using silica gel chromatography to obtain compound 2.

Example 3

Synthesis of Compound 3

Compound 3 described below was synthesized.

[Formula 15]

(Compound 3)

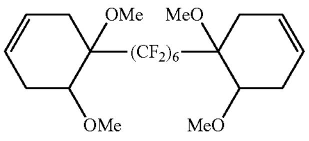

Compound 3 was synthesized from compound 2 above in the following procedure.

Sodium hydride (0.072 g, 3 mmol) and tetrahydrofuran (7 mL) were prepared in a 30 mL two mouth flask having an agitator installed in an argon atmosphere, compound 2 (0.277 g, 0.5 mmol) was dissolved in tetrahydrofuran (2 mL) while agitating at 0° C. and added dropwise, and this was agitated for 30 minutes at 0° C. After dissolving iodomethane (0.426 g, 3 mmol) in tetrahydrofuran (1 mL) and adding dropwise, the temperature was increased to room temperature and this was agitated for 21 hours. The reaction solution was diluted using hexane, and after adding a saturated ammonium chloride aqueous solution, organic material was extracted from the water layer using hexane, and the organic layer was dried using anhydrous sodium sulfate. The anhydrous sodium sulfate was removed by filtration and concentrated under reduced pressure, and the obtained concentrate was then purified using silica gel chromatography to obtain compound 3.

Example 4

Synthesis of Compound 4

Compound 4 described below was synthesized.

[Formula 16]

(Compound 4)

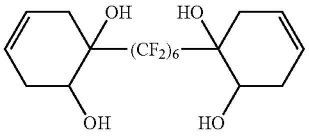

Compound 2 above (0.291 g, 0.5 mmol) and methylene chloride (5 mL) were prepared in a 30 mL two mouth flask having an agitator installed in an argon atmosphere, boron tribromide (1M: methylene chloride solvent, 5 mL, 5 mmol) was added, and this was agitated for 3 hours at room temperature. Ammonia water was added at 0° C. and this was agitated for 30 minutes. Organic material was extracted from the water layer using methylene chloride, and the organic layer was washed using a saturated saline solution and dried using anhydrous sodium sulfate. The anhydrous sodium sulfate was removed by filtration, and after the organic layer was concentrated under reduced pressure, the obtained concentrate was then purified using silica gel chromatography to obtain compound 4.

Example

It was confirmed that the structure represented by Formula (1) of the present application forms the desired cross-linked structure in the following tests.

Compound 2A described below having the structure of compound 2 above was used as the crosslinking agent. Furthermore, because fluoroalkyl iodide ($-CF_2CF_2I$) is introduced on the crosslinking reaction site of fluoroelastomer, tridecafluoroiodide was used in tests instead of perfluoroelastomer. Both were made to react in the presence of a radical initiator, and compound 2B below was synthesized, having the cyclohexene ring of compound 2A converted to a cyclohexane ring. Thereafter, compounds 2C and 2C' below were synthesized, having the cyclohexane ring of compound 2B converted to an aromatic ring by heat. Thus, it was confirmed that the crosslinking agent of the present application undergoes a crosslinking reaction with fluoroelastomer and then undergoes aromatization due to heating thereafter. Note that in example 2, the compound 2A can be synthesized using tridecafluoroiodide instead of 1,6-diiodododecafluorohexane.

[Formula 17]

(Compound 2A)

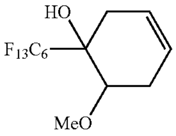

(Compound 2B)

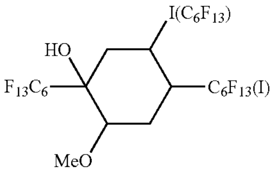

(Compound 2C)

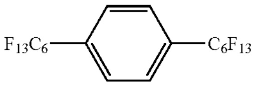

(Compound 2C')

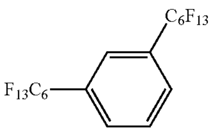

Compound 1 (0.444 g, 1.0 mmol), ethylene dichloride (3.3 mL), and tridecafluorohexyl iodide (1.326 g, 3.0 mmol) were prepared in a 20 mL two mouth flask having an agitator installed in an argon atmosphere, benzoyl peroxide (0.102 g, 0.30 mmol) was added and this was agitated for 24 hours at 90° C. After returning to room temperature, the obtained concentrate was purified using silica gel chromatography to obtain compound 2B.

Compound 2B (0.089 g, 0.10 mmol) and pyridine (1.0 mL) were prepared in a 20 mL two mouth flask having an agitator installed in an argon atmosphere, thionyl chloride (0.026 g, 0.22 mmol) was slowly added, and this was then agitated for 18 hours at room temperature. After diluting using ether and washing the organic layer using dilute hydrochloric acid, a sodium hydrogen carbonate aqueous solution, and pure water in this order, this was then dried using anhydrous sodium sulfate. The anhydrous sodium sulfate was removed by filtration, and after the organic layer was concentrated under reduced pressure, the obtained concentrate was then purified using silica gel chromatography to obtain compound 2C and compound 2C'.

Structural Analysis of Compound 2B $^1$H-NMR ($CDCl_3$, 400 MHz): δ=1.70 to 3.59 (m, 9H), 3.59 to 4.09 (m, 1H), 4.21 to 4.82 (m, 1H)

$^{19}$F-NMR ($CDCl_3$, $CFCl_3$, 376 MHz): δ=81.12 to 81.35 (m, 6F), 106.10 to 124.41 (m, 16F), 125.32 to 128.00 (m, 4F)

Structural Analysis of Compound 2C $^1$H-NMR ($CDCl_3$, 400 MHz): δ=7.76 (s, 4H)

$^{19}$F-NMR ($CDCl_3$, $CFCl_3$, 376 MHz): δ=−81.26 (t, J=19.50 Hz, 3F), −111.77 (t, J=28.46 Hz, 2F), −121.71 to −122.08 (m, 2F), −122.12 to −122.33 (m, 2F), −123.18 to 123.46 (m, 2F), −126.52 to −126.74 (m, 2F)

Structural Analysis of Compound 2C'

$^1$H-NMR ($CDCl_3$, 400 MHz): δ=7.70 (t. J=7.76 Hz, 1H), 7.82 (s, 2H), 7.84 (s, 1H)

$^{19}$F-NMR ($CDCl_3$, $CFCl_3$, 376 MHz): δ=−81.49 (t, J=19.69 Hz, 3F), −111.78 (t, J=28.73 Hz, 2F), −121.81 to −122.18 (m, 2F), −122.37 to −122.68 (m, 2F), −123.23 to 123.59 (m, 2F), −126.67 to −126.92 (m, 2F)

Example 5 and Comparative Examples 1 and 2

Synthesis of Compound 5

Compound 5 described below was synthesized.

[Formula 18]

(Compound 5)

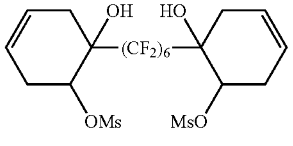

Compound 4 above (0.080 g, 0.15 mmol), methylene chloride (15 mL), triethylamine (0.090 g, 0.9 mmol), and 4-dimethylaminopyridine (2 mg, 0.015 mmol) were prepared in a 30 mL two mouth flask having an agitator installed in an argon atmosphere, and this was cooled to 0° C. Trifluoromethanesulfonyl chloride (0.103 g, 0.9 mmol) was added dropwise thereto, and this was agitated for 20 hours at 40° C. The reaction vessel was returned to room temperature and the reaction was stopped using ammonia water. Organic material was extracted from the water layer using methylene chloride, and the organic layer was washed using a saturated saline solution and dried using anhydrous sodium sulfate. The anhydrous sodium sulfate was removed by filtration, and after the organic layer was concentrated under reduced pressure, the obtained concentrate was then purified using silica gel chromatography to obtain compound 5.

Sample Manufacturing Method

Each sample was prepared as in Table 2 below.

Each component of the added amounts shown in Table 2 were inserted in a pressure-resistant vessel and substituted with Ar. This was then left until the perfluoroelastomer (PFE 40z made by 3M) dissolved. The pressure-resistant vessel was heated to 100° C.×30 mins to crosslink FFKM. This was then heated at 130° C.×2 hrs in a vacuum oven to volatilize the solvent. This was then heated at 310° C.×4 hours in a nitrogen-substituted oven.

TABLE 2

Table 2

| | Example 5 | Comparative Example 1 | Comparative Example 2 |
|---|---|---|---|
| Perfluoroelastomer | 0.5 g | 0.5 g | 0.5 g |
| Crosslinking Initiator (Benzoyl Peroxide) (NYPER BW made by NOF Corporation) | 0.03 mmol | 0.03 mmol | 0.03 mmol |
| Compound (5) | 0.06 mmol | | |
| Crosslinking Agent (d) of Patent No. 6374867 | | 0.06 mmol | |
| Triallyl Isocyanurate (TAIC made by Shinryo) | | | 0.06 mmol |
| Solvent (Fluorinert FC-3283) | 5 ml | 5 ml | 5 ml |

[Vapor Resistance Evaluation]

The weight (A) of the sample created in the method above (crosslinked molded product) was measured and exposed to saturated steam at 330° C. for 24 hours. The vapor exposed sample was immersed in Fluorinert FC-3283 at room temperature for 72 hours. The sample remaining as solid content after soaking was removed and heated at 130° C.×2 hrs in a vacuum oven to volatilize the solvent. The weight (B) after drying was measured, and the gel fraction was calculated using the following formula. The results are shown in Table 3.

$$\text{Gel fraction}=\text{mass (B)}/\text{mass (A)}\times 100$$

TABLE 3

Table 3

| | Gel Fraction |
|---|---|
| Example 5 | 50% |
| Comparative Example 1 | 30% |
| Comparative Example 2 | 0% |

INDUSTRIAL APPLICABILITY

The compound of the present invention can be used as the crosslinking agent of a fluoroelastomer. The crosslinked fluoroelastomer of the present invention may be used as a sealing material (O ring, etc.) that demands chemical resistance and high-temperature vapor resistance such as in power generation, semiconductor devices, and chemical plants.

The invention claimed is:

1. A composition containing a fluoroelastomer, a crosslinking initiator, and a crosslinking agent containing a compound having the structure represented by the following Formula (1):

(1)

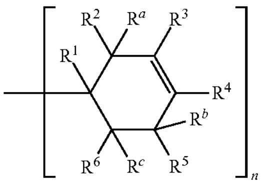

wherein $R^1$ to $R^6$ are each a hydrogen atom, a substituent, or a leaving group, and two or more of $R^1$ to $R^6$ are leaving groups; $R^a$ to $R^c$ are each a hydrogen atom or a substituent;

and n is an integer from 2 to 5.

2. A crosslinked fluoroelastomer obtained by crosslinking the composition according to claim 1.

3. A method for producing a crosslinked fluoroelastomer, comprising a step for heating the composition according to claim 1 to react the fluoroelastomer with the crosslinking agent and a step for converting a cyclohexane ring derived from the crosslinking agent into an aromatic ring.

4. A crosslinked fluoroelastomer produced by the method in claim 3, wherein a gel fraction after being exposed to 330° C. saturated steam for 24 hours is 45% or more.

5. A molded product obtained from a crosslinked fluoroelastomer obtained by crosslinking a composition containing a fluoroelastomer, a crosslinking initiator, and a crosslinking agent containing a compound having the structure represented by the following Formula (I);

(1)

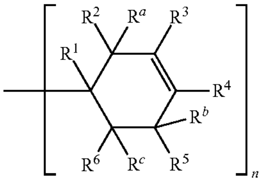

wherein $R^1$ to $R^6$ are each a hydrogen atom, a substituent, or a leaving group, and two or more of $R^1$ to $R^6$ are leaving groups; $R^a$ to $R^c$ are each a hydrogen atom or a substituent; and n is an integer from 2 to 5.

6. The molded product according to claim 5, being a sealing material.

7. A crosslinked fluoroelastomer having a crosslinked structure represented by the following formula:

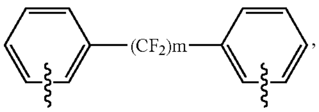

wherein m is an integer from 1 to 15;

a gel fraction after being exposed to 330° C. saturated steam for 24 hours is 45% or more;

the crosslinked structure does not contain any unsaturated bonds other than those in aromatic rings; and the squiggly lines represent attachment points to one or more other fluoroelastomers having the formula

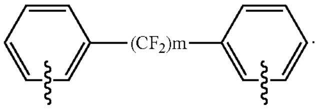

* * * * *